(12) United States Patent
Richter et al.

(10) Patent No.: US 6,844,089 B2
(45) Date of Patent: Jan. 18, 2005

(54) ORGANIC RED ELECTRO-LUMINESCENT DEVICE AND DOPANT

(75) Inventors: Andreas Richter, Ploessnitz (DE); Dietmar Keil, Wolfen (DE); Gerhard Diener, Köthen (DE)

(73) Assignee: Sensient Imaging Technologies GmbH, Wolfen (DE)

( * ) Notice: Subject to any disclaimer, the term of this patent is extended or adjusted under 35 U.S.C. 154(b) by 0 days.

(21) Appl. No.: 10/143,507

(22) Filed: May 10, 2002

(65) Prior Publication Data

US 2003/0232215 A1 Dec. 18, 2003

(51) Int. Cl.[7] .......................... H05B 33/14; C09K 11/06; C07D 221/02; C07D 471/12
(52) U.S. Cl. ...................... 428/690; 428/917; 313/504; 313/506; 546/82; 546/94; 546/98; 544/250; 544/252
(58) Field of Search ................................ 428/690, 917; 313/504, 506; 252/301.16; 257/102; 546/82, 94, 98, 99; 544/250, 252

(56) References Cited

U.S. PATENT DOCUMENTS

| | | | |
|---|---|---|---|
| 2,965,486 A | 12/1960 | Brooker et al. ............... | 96/105 |
| 3,511,831 A | 5/1970 | Dunbar et al. ............... | 260/240 |
| 3,852,683 A | 12/1974 | Webster et al. ......... | 331/94.5 L |
| 4,047,948 A | 9/1977 | Horgan ...................... | 96/1.5 R |
| 4,175,960 A | 11/1979 | Berwick et al. ............... | 430/58 |
| 4,539,507 A | 9/1985 | Van Slyke et al. .......... | 313/504 |
| 4,769,292 A | 9/1988 | Tang et al. ................. | 428/690 |
| 5,061,569 A | 10/1991 | VanSlyke et al. ........... | 428/457 |
| 5,166,339 A | 11/1992 | Duff et al. .................. | 540/141 |
| 5,283,132 A | 2/1994 | Ogura et al. ................ | 428/690 |
| 5,359,072 A | 10/1994 | Mignani et al. .............. | 546/94 |
| 5,535,048 A | 7/1996 | Mignani et al. .............. | 359/326 |
| 5,908,581 A | 6/1999 | Chen et al. ............ | 252/301.16 |
| 5,935,720 A | 8/1999 | Chen et al. ................. | 428/690 |
| 6,020,078 A | 2/2000 | Chen et al. ................. | 428/690 |
| 6,025,894 A | 2/2000 | Shirasaki et al. ............. | 349/69 |
| 6,329,086 B1 | 12/2001 | Shi et al. .................... | 428/690 |
| 6,451,456 B1 | 9/2002 | Kim et al. ................... | 428/690 |
| 2002/0164498 A1 | 11/2002 | Chen et al. .................. | 428/690 |
| 2003/0044644 A1 | 3/2003 | Kim et al. ................... | 428/690 |
| 2003/0098861 A1 | 5/2003 | Lee et al. ................... | 428/690 |
| 2003/0162054 A1 | 8/2003 | Chen et al. .................. | 428/690 |
| 2003/0176520 A1 | 9/2003 | Taniguchi et al. ............. | 522/26 |

FOREIGN PATENT DOCUMENTS

| | | |
|---|---|---|
| DE | 23 45 189 | 3/1975 |
| DE | 28 31 054 A1 | 1/1979 |
| DE | 689 19 989 T2 | 5/1995 |
| DE | 195 41 113 A1 | 4/1997 |
| EP | 0 244 051 A2 | 11/1987 |

OTHER PUBLICATIONS

Su–Jin Park et al., "A Molecular Orbital Study on the Optical Properties of Fluorescent Dyes", Mat. Res. Soc. Symp. Proc. vol. 677, pp. AA7.4.1–AA7.4.6 (Sep. 2001).*

X. T. Tao, S. Miyata, H. Sasabe, G.J. Zhang, T. Wada, M.H. Jiang, "Efficient Organic Red Electroluminescent Device with Narrow Emission Peak," Applied Physics Letters, vol. 78, No. 3, Jan. 15, 2001, pp. 279–281.

C.W. Tang, "Organic Electroluminescent Diodes," Applied Physics Letters, vol. 51, No. 12, Sep. 21, 1987, pp. 913–915.

Ralf Lemke, "Knoevenagel–Kondensationen in Dimethyl-formamid," International Journal of Methods in Synthetic Organic Chemistry, May 1974, pp. 359–361.

Ralf Lemke, "Solvatochromie von 80 mµ in verschiedenen Alkoholen bei Arylidenisophoron–Abkömmlingen," Chemische Berichte Jahrg. vol. 103, Jun. 1970, pp. 1894–1899.

H. Katayama, M. Ohkoshi, "International Journal of Methods in Synthetic Organic Chemistry," Aug. 1982, pp. 692–693.

Kari Skinnemoen, Kjell Undheim, "Synthesis of 2H–Pyran–3–(6H)–ones," Acta Chemica Scandinavica, Series B, 1980, pp. 295–297.

\* cited by examiner

*Primary Examiner*—Marie Yamnitzky
(74) *Attorney, Agent, or Firm*—Foley & Lardner LLP

(57) ABSTRACT

The invention relates to an electroluminescent device, in which the luminescent layer contains a luminescent compound and a compound of the general formula I as doping agent, wherein B is an unsaturated carbocyclic or heterocyclic 4–8-link ring, which can also contain an alicyclic bridge, the rings D and E are five- or six-link rings, which each can contain one more hetero-atom N, O and S, the radicals R are one or more substituents H or straight-chain or branched $C_1$–$C_6$-alkyl, X and Y are carbon or nitrogen, $R_1$; $R_2$ and $R_9$ are H or straight-chain or branched $C_1$–$C_6$-alkyl, $R_3$ and $R_9$ are hydrogen, straight-chain or branched $C_1$–$C_6$-alkyl, hydroxy, —$OR_{16}$, —$COOR_{16}$, N,N-dialkylamino, acetylamino or halogen, wherein $R_{16}$ is hydrogen, or straight-chain or branched $C_1$–$C_6$-alkyl, $R_1$ and $R_2$ or $R_2$ and $R_3$ and/or $R_9$ and $R_9$ together can form an alicyclic, heterocyclic or aromatic ring, and $A_1$ and $A_2$, which can be the same or different, are cyan, nitro or —$COOR_{16}$. The compounds I are partly new. Together with the luminescent compound, the doping agents have a red or white color, depending on the concentration, with excellent quantum efficiency.

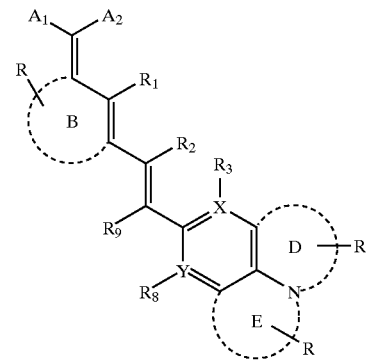

43 Claims, 2 Drawing Sheets

ORGANIC RED ELECTRO-LUMINESCENT DEVICE AND DOPANT

The invention relates to an organic, particularly, red electroluminescent device, specifically, a device with a luminescent layer, containing at least one luminescent compound or, additionally, a doping agent as well as new compounds.

Figure 1:
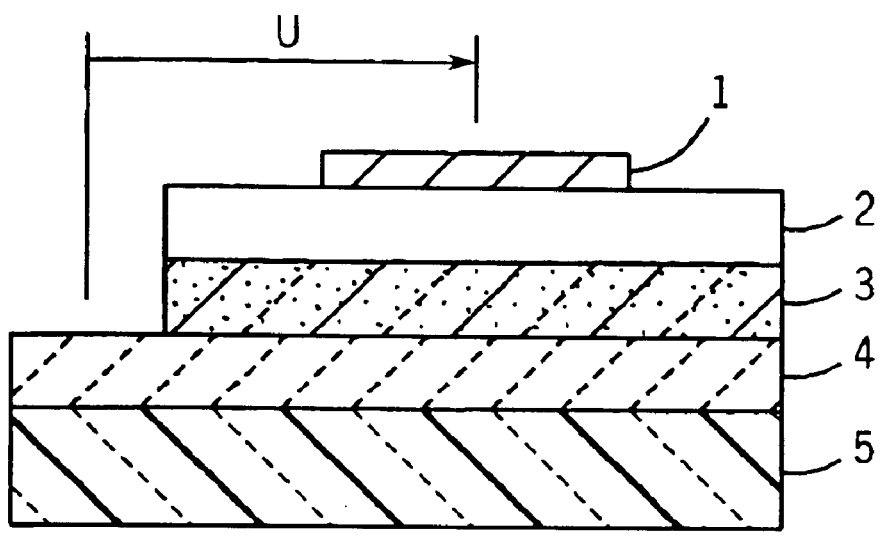

Organic electroluminescent devices have been known for quite some time and, in the simplest case, consist of a glass substrate with a transparent indium tin oxide (ITO) coating, a hole transport layer, followed by a luminescent layer as well as a metal electrode with low electron emission (see FIG. 1).

In this case, electrons are injected in the transitory direction of the metal electrode (cathode), which is usually made of Ca or Mg; and produced through co-vaporization or successive vaporization, (for example with Al or Ag). Electrons from the hole (hole electrons) are injected into the organic multi-layer composite by the transparent ITO contact (anode). These recombine there and form singlet excitons, which, after a short period of time change to the ground level state after emission of light. The organic inter-laminar bonding, consists, in this case, of a luminescent layer (including a luminescent compound which is simultaneously also an electron conductor) and a hole transport layer. In the hole transport layers, preferably N,N'-biphenyl-N,N'-bis-(m-tolyl)benzidine (TPD) and N,N'-biphenyl-N,N'-bis-(1-naphthyl)-benzidine (1-NPB) are used as hole transport materials. The extra addition of an electron transport layer frequently leads to increased quantum efficiency and/or a reduced inception voltage of the electroluminscent device (see FIG. 2).

At the same time, the luminescent layer can have a very thin design. By utilizing luminescent material independent of its transport characteristics, the emission wavelength can be specifically adjusted over the entire visible spectrum. Furthermore the properties of the electroluminescent device are improved (increased quantum efficiency and reduced electroluminescence inception voltage) if at least two of the used hole transport layers are attuned to each (see FIG. 3).

In some cases, an electron transport layer (such as in FIG. 2) can be additionally applied between the luminescent layer and the metal electrode.

Recently an additional thin hole injection layer, for example, of CUPC (copper phthalocyanine), has also been applied through vapor deposition between the transparent ITO and the hole transport layer (see FIG. 4) to improve the properties of electroluminescent devices. In particular so-called "Starburst Molecules" are used in the second hole transport layer due to their low ionization potential. These are highly molecular organic compounds on the basis of tri-phenylamine units.

Recently a novel hole transport material was described in DE-A-19,541,113 which, apart from good hole transport properties, also exhibits excellent layer-forming characteristics, high thermal stability and thus a low tendency towards recrystallization.

For the production of full color-capable electroluminescent devices it is necessary to use red, green and blue electroluminescent materials with high electroluminescence quantum efficiency and color purity.

For quite some time, tris-(8-hydroxyquinolino)-aluminum ($AlQ_3$) has been used as the preferred luminous material in the luminescent layer (C. W. Tang, S. A. van Slyke: Appl. Phys. Lett. 51, 1987, 913). This metal chelate complex in itself is a luminescent green in the inter-laminar bonding, wherein also beryllium or gallium can be used as metals in the complex.

Blue electroluminescent devices are obtained by using derivatives of the 1,3,4-oxidiazo or by using distyryl-arylenes. Red luminescent radiation is achieved in particular by doping $AlQ_3$ with 2-alkyl-6-N,N-dialkyl amine styryl substituted 4-dicyanomethylene-4H-pyrans especially, however, with the 2-methyl-6-(4-N,N-dimethylaminostyryl)$_4$ dicyanomethylene-4H-pyran (DCM) (U.S. Pat. No. 4,769,292), but also with dihydroxy cyclobutene dione dyes second power acidic dyes.

To name the disadvantage in the usage of DCM as a doping agent of $AlQ_3$ is that the emitted light appears too orange to the human eye, the efficiency of the emitted light is not sufficiently high for many applications due to aggregation effects of the DCM dye in the $AlQ_3$ and thus the light-emitting diodes additionally do not work with a sufficient long term stability.

DCM, which has already become known as a laser dye, (U.S. Pat. No. 3,852,683) and additional dyes derived from it, represent formally conjugated polyenic combinations with a donor/acceptor substituent pattern. By varying the donor substituents in the dye molecule, such as, for example, by replacing the 4-N,N-dimethylaminophenyl radical in the DCM with the considerably stronger donor julolidine radical (DCJ dye), long-wave absorption bands shift, and parallel to it also the emission band batho-chrome with respect to the DCM. When utilizing DCJ in electroluminescent compounds, then the visual color impression also corresponds to a more intensive red.

The disadvantageous aggregation tendency in the application area of the doping agent >1 percent by weight with respect to $AlQ_3$, however, is also maintained in this case so that these materials create too little efficiency in electroluminescent devices. Additionally, poor vaporization ability of the compound, when using DCJ, should be pointed out. The high decomposition rate during the vaporization process leads above all to problems in the manufacture of the luminescent layer as such.

Although the introduction of bulky tert.-butyl substituents in the 2-position of the pyran ring of corresponding DCM-analog dyes, as described in U.S. Pat. No. 5,935,720, reduces the aggregation tendency for example of the dyes DCJT and DCJTB compared to DCJ or DCM, this tendency cannot be sufficiently suppressed either in order to make materials available for full color suitable applications.

The disadvantage with all doping agent/$AlQ_3$ systems, in addition to the already named effects, is the visually impure color impression (color tone) of the emitted light, which is frequently perceived by the human eye only as a dull orange-red to red. The reasons for this are apparently the existence of two conjugation directions, respectively, which are characteristic for this category of dyes. On the one hand, the main conjugation direction of these "D/A dyes" leads from the donor substituent D via the polyenic chain to the acceptor A (here a cyano-group) in the 4-position of the pyran ring and, on the other hand, via a short conjugation chain from a positive mesomeric substituent in the 2-position on the pyran ring (can be a phenyl or a substituted phenyl ring) or from a positive inductive substituent on the same position (can be an alkyl or branched alkyl group) also towards the acceptor substituent in the 4-position of the pyran ring. This quasi-crossed conjugation already provides broad absorption and emission bands and thus impure color tones of the emitted light.

Recently X. T. Tao, S. Miyata, H. Sasabe, G. J. Zhang, T. Wada, M. H. Jiang (Appl. Physics Letters 78, 2001, 279–281) showed that by using 3-dicyanomethylene)-5,5-dimethyl-1-(4-N,N-dimethyl amino-styryl)-cyclohexene (DCDDC) as the doping agent for $AlQ_3$ instead of dyes on DCM-basis in the electroluminescent layer, a considerably purer and more intensive light emission can be achieved. Due to only one possible conjugation direction in this type of dye, the absorption and emission bands are very narrow. At 1% doping of $AlQ_3$, the above-mentioned materials, however, have already reached their maximum electroluminescence quantum efficiency with respect to $AlQ_3$ since here, as well, higher doping leads increasingly to the formation of aggregates.

The optimal concentration for these systems of the doping agents in the range of <1 percent by weight, referred to $AlQ_3$, is too low so that due to insufficient energy transmission, the inherent luminescence of $AlQ_3$ distorts the color impression of the resulting emitted light. Impure red color tones are again the consequence so that the initially revealed advantage of these dyes compared to the DCM types is largely lost.

It was the task of the invention, to make an organic electroluminescent device with improved quantum efficiency and improved long-time stability available and thus to develop new luminescent compounds for the luminescent layer and new doping agents for familiar luminescent compounds, especially for $AlQ_3$. Another objective was to make available new compounds.

According to the invention, the electroluminescent device consists of at least one hole transport layer and one luminescent layer between two conductive electrodes, wherein at least one electrode is transparent, and it is characterized by the fact that the luminescent layer contains at least one compound of the general formula I as the luminescent compound or as doping agent for a luminescent compound,

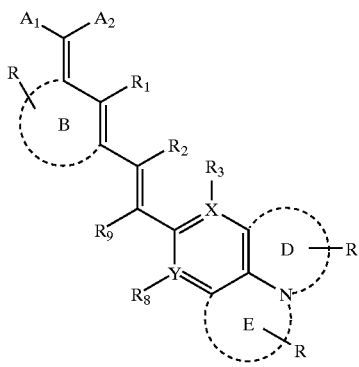

I wherein
B represents an unsaturated carbo-cyclic or hetero-cyclic 4–8-link ring with O, N or S as hetero-atom, wherein in the case of a 6–8-link ring two C-atoms in this ring can be bridged, i.e. they can form a bridge;
the D and E—rings are five- or six-link rings, each of which can contain an additional hetero-atom, selected from N, O and S;
the radicals R are one or more substituents, which can be the same or different and are hydrogen or straight-chain or branched $C_1$–$C_6$-alkyl;
X and Y are carbon or nitrogen;
$R_1$, $R_2$ and $R_9$ are the same or different and are hydrogen or straight-chain or branched $C_1$–$C_6$-alkyl or halogen, in particular hydrogen or methyl or fluorine;
$R_3$ and % are the same or different and are hydrogen, straight-chain or branched $C_1$–$C_6$-alkyl, hydroxy, —$OR_{16}$, —$COOR_{16}$, N,N-dialkylamino, acetylamino or halogen, wherein $R_{16}$ is hydrogen, or straight-chain or branched $C_1$–$C_6$-alkyl,
$R_1$ and $R_2$ or $R_2$ and $R_3$ and/or $R_8$ and $R_9$ together can form an alicyclic, heterocyclic or aromatic ring, and
$A_1$ and $A_2$, which can be the same or different, are cyan, nitro or —COO $R_{16}$, wherein $R_{16}$ takes on the above-mentioned designation.

A particular embodiment of the invention relates to electroluminescent devices, which contain a compound of the general formula II as doping agent, either alone or in a mixture with other doping agents,

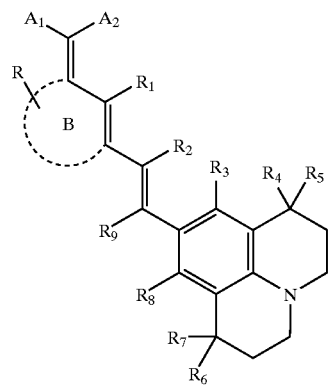

II wherein $R_1$, $R_2$, $R_4$ to $R_7$ and $R_9$ are the same or different and are hydrogen, or straight-chain or branched $C_1$–$C_6$ alkyl, $R_3$ and are the same or different and are hydrogen, straight-chain or branched $C_1$–$C_6$-alkyl, hydroxy, —$OR_{16}$, —$COOR_{16}$, N,N-dialkylamino, acetylamino or halogen, wherein $R_{16}$ is hydrogen or straight-chain or branched $C_1$–$C_6$-alkyl,
$R_1$ and $R_2$ or $R_2$ and $R_3$ and/or $R_8$ and $R_9$ together can form an alicyclic, heterocyclic or aromatic ring, and
B is a five- or six-link unsaturated ring, where in the case of a 6-link ring, two ring atoms in the 1,3-position can form an alicyclic bridge with each other, and the radicals R are one or more substituents, which can be the same or different and are hydrogen or straight-chain or branched $C_1$–$C_6$-alkyl;
$A_1$ and $A_2$, which can be the same or different, are cyan, nitro or $COOR_{16}$, wherein $R_{16}$ is hydrogen or straight-chain or branched $C_1$–$C_6$-alkyl.

Preferred radicals R through $R_9$ in their meaning as low alkyl radicals ($C_1$–$C_6$) are such that represent methyl, isopropyl or tert-butyl, respectively.

Another preferred design type relates to a device in which a compound of the general formula III or the general formula IV is contained as doping agent,

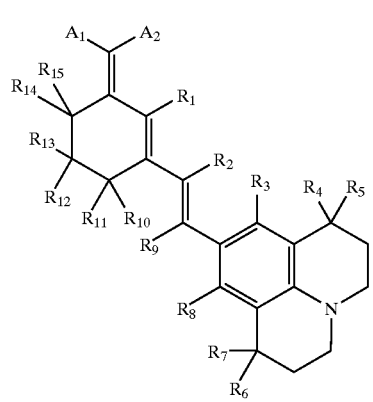

III

-continued

IV wherein $R_{10}$ through $R_{15}$ are hydrogen, straight-chain or branched $C_1$–$C_6$-alkyl, preferably methyl, and the other radicals which have the above-mentioned significance. $R_{10}$ and $R_{15}$ can form an alicyclic bridge, such as e.g. in the dye 2 or 4, as necessary, see Table I further below.

The organic electroluminescent device, in its simplest case, is made of a multi-layer composite in accordance with FIG. 1, consisting of a metal electrode 1 (cathode), of a luminescent layer 2, which apart from an organic luminescent compound, in particular $AlQ_3$, contains at least one organic doping agent, of a hole transport layer 3, which contains an organic hole transport compound, of a transparent conductive anode 4 as well as of a carrier made of glass or a similar transparent material. In a different set-up of the electroluminescent device, such as e.g. in accordance with FIG. 2, with an additional electron transport layer 6 and, in accordance with FIG. 3, with two hole transport layers 3a and 3b, the properties of this device can be optimized. Another layer is possible, e.g. a thin CuPC layer between the conductive transparent layer 4 and the hole transport layer 3.

The compound of formula I or of formula II also exists advantageously as a doping agent in a mixture with other doping agents, which can be selected from the group consisting of 2-alkyl-6-N,N-dialkylaminostyryl- or julolidine-substituted 4-dicyanomethylene-4-H-pyrans, corresponding to pyrans substituted with tert-butyl on the pyran ring and 3-(dicyanomethylene)-5,5-dimethyl-1-(4-N,N-dimethylamino-styryl)cyclohexane, in particular with a 1,2- or 1-3-substituted dihydroxycyclobutene-dione dye. The joint usage of several doping agents can occur e.g. through co-vaporization.

The organic luminescent compound is preferably selected from tris-(8-hydroxyquinolino)-aluminum ($AlQ_3$), derivatives of the 1,3,4-oxadiazo and distyryl-aryl derivatives, wherein ($AlQ_3$) is particularly preferred.

It has been determined that novel and familiar compounds used recently in electroluminescent devices in a concentration range of >1 percent by weight to 8 percent by weight, preferably >1 to 5 percent by weight, in particular 1.5–3 percent by weight, with respect to the weight of the organic luminescent compound $AlQ_3$, create a very efficient pure red light alone or together with $AlQ_3$ with luminance in the range of 570 to 2100 cd/m² at 10 to 14V, in particular 580 to 2050 cd/m² at 10.2 to 13.8V. This occurs without secondary emission of $AlQ_3$ in the range around 530 nm.

The increased concentration range with doping agents, compared to familiar electroluminescent devices, leads to light of considerably higher quality where the inherent luminescence of the luminescent compound, e.g. $AlQ_3$, does not distort the red color tone.

Furthermore, the surprising finding was made that the organic electroluminescent device in the case of "under-doping" of a luminescent device, in particular with under-doping of $AlQ_3$, emits white light with the doping agents to be used pursuant to the invention. Under-doping exists when the doping agent is used alone or in a mixture with different doping agents in a concentration between 0.1 percent by weight and 0.8 percent by weight, particularly between 0.1 percent by weight and 0.5 percent by weight, referred to the weight of $AlQ_3$, e.g. by co-vaporizing both.

Without intermediate ventilation, the metal cathode 1 is finally applied through a vapor deposition process by vaporizing LiF or Li-benzoate and Al, generally at a ratio of 10:1 (0.7 nm Li-benzoate+100 nm Al). However, other metals, such as silver, magnesium, calcium or indium, or alloys thereof, or different ratios of the metals or alloys, can also be used.

The object of the invention consists also of new compounds of the general formula I

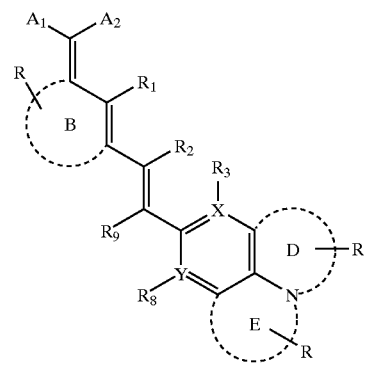

I wherein B is a 4-, 5-, 7- or 8-link unsaturated carbocyclic ring, which is substituted by hydrogen and/or $C_1$–$C_6$-alkyl and, in the case of a 5-link ring carries at least one $C_1$–$C_6$-alkyl radical; or B is possibly a 6-link unsaturated carbocyclic ring, substituted by one or more straight-chain or branched $C_1$–$C_6$-alkyl groups, where two ring atoms in the 1,3-position can form an alicyclic bridge with each other; or B is a 6-link unsaturated carbocyclic ring, which is substituted by one or more $C_1$–$C_6$-alkyl groups; or B is an unsaturated heterocyclic 4- to 8-link ring with O, N or S as hetero-atom, which is substituted by hydrogen and/or one or more $C_1$–$C_6$-alkyl groups;

the rings D and E are five- or six-link rings, each of which can contain one more hetero-atom, selected from N, O and S with the specification that at least one of the two rings contains another hetero-atom; and the radicals R are one or more substituents, which can be the same or different and are hydrogen for straight-chain or branched $C_1$–$C_6$-alkyl;

X and Y can be carbon or nitrogen;

$R_1$, $R_2$ and $R_9$ are the same or different and are hydrogen or straight-chain or branched $C_1$–$C_6$-alkyl;

$R_3$ and h are the same or different and are hydrogen, straight-chain or branched $C_1$–$C_6$-alkyl, —$COOR_{16}$, N,N-dialkyl amino, acetylamino or halogen, wherein $R_{16}$ is hydrogen, or straight-chain or branched $C_1$–$C_6$-alkyl, $R_1$ and $R_2$ or $R_2$ and $R_3$ and/or $R_8$ and $R_9$ together can form an alicyclic, heterocyclic or aromatic ring, and $A_1$ and $A_2$, which can be the same or different, are cyan, nitro or —$COOR_{16}$, wherein $R_{16}$ is hydrogen, or straight-chain or branched $C_1$–$C_6$-alkyl.

A specific design of the invention is represented by the compounds of the general formula 1, wherein B is a 5-link unsaturated carbocyclic ring and the rings D and E are six-link carbocyclic rings, which are substituted by $C_1$–$C_6$-alkyl groups; or wherein B is a six-link unsaturated carbocyclic ring, which may be substituted by one or more straight-chain or branched $C_1$–$C_6$-alkyl groups, where two ring atoms in the 1,3-position can form an alicyclic bridge with each other with the structure

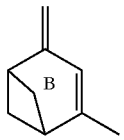

and the rings D and E are six-link carbocyclic rings, which are substituted by hydrogen and/or $C_1$–$C_6$-alkyl groups, and wherein X and Y represent carbon.

Preferred radicals R through $R_9$ in the designation of $C_1$–$C_6$-alkyl are methyl, isopropyl or tert-butyl.

Production of the electroluminescent device generally occurs in such a way that initially the dye to be used as luminescent compound, however the doping agent in particular, is produced by preparing it, for example, from isophoron, verbenon or another cyclic 1-methyl-vinylketone with malonimt and corresponding 9-formyl julolidine while employing a Knoevenagel catalyst in an aprotically dipolar solvent, such as DMF, possibly without separation of intermediate products that form, isolating it, pre-cleaning it through recrystallization and, finally, obtaining it in its purest form through sublimation in a high vacuum. Then, for example, this dye is applied as a luminescent compound or as doping agent of a luminescent compound, possibly in a mixture with additional different doping agents, onto a conductive transparent (ITO) carrier that has been vaporized with one or more hole transport layers or it is applied together with a luminescent substance, preferably with $AlQ_3$, in a high vacuum, e.g. through co-vaporization, onto a conductive transparent (ITO) carrier that has been coated with one or more hole transport layers aromatic ring, and through spin coating.

The multi-layer composite obtained this way can be equipped with additional layers, if necessary, such as an electron transport layer. Subsequently the metal cathode is applied through vaporization of particularly Li-benzoate and Al.

The drawings depict:

FIG. 1: simple multi-layer composite of an electroluminescent device

Figure 2:
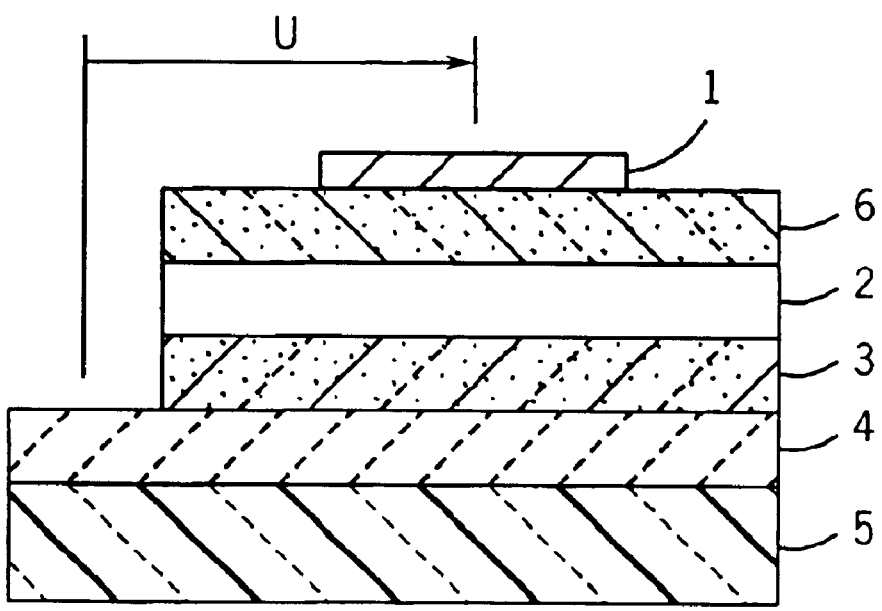

FIG. 2: multi-layer composite with additional electron transport layer

Figure 3:
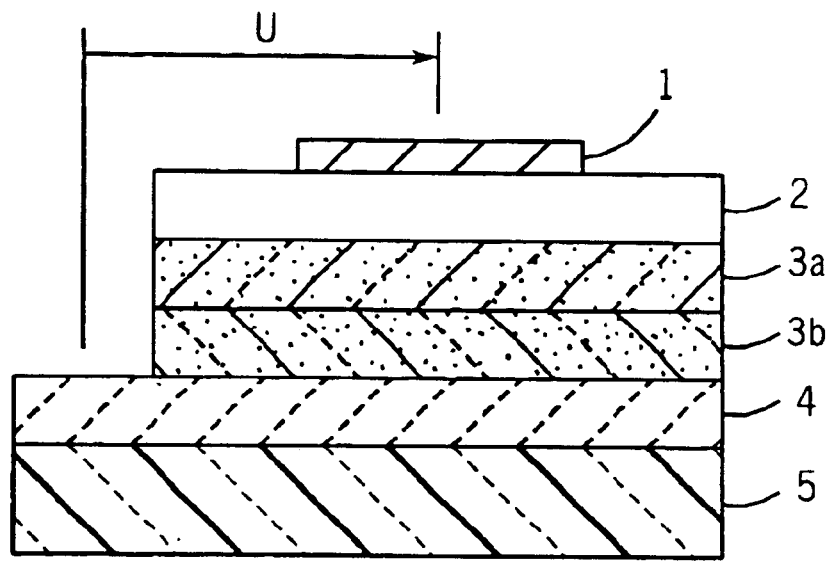

FIG. 3: multi-layer composite with additional hole transport layer

Figure 4:
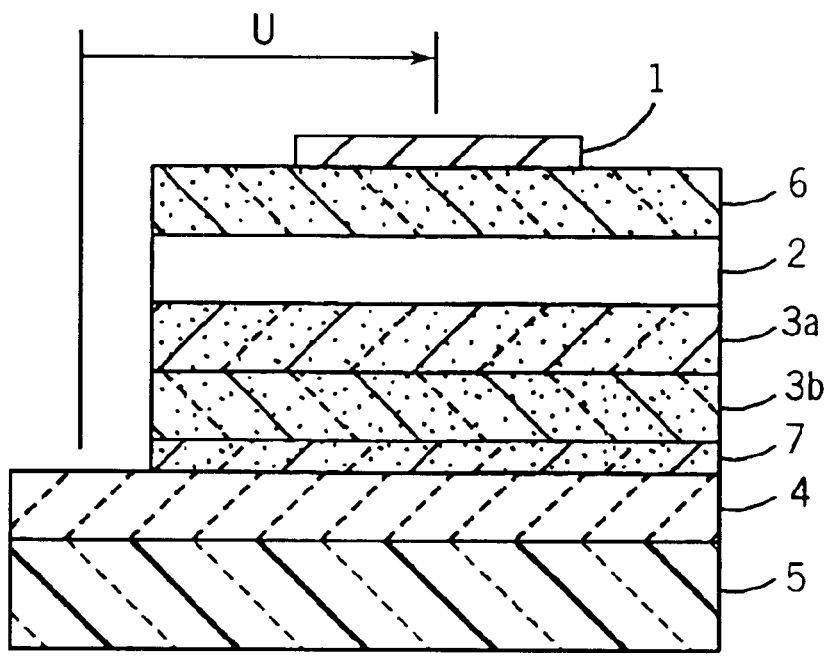

FIG. 4: multi-layer composite with additional hole injection layer

In the drawing, U represents the tension that is applied between the corresponding electrodes.

Individually, the production proceeds in such a way that in the device that is to be used in accordance with the invention, first the anode is applied onto a stable glass carrier as a transparent conductive layer of indium tin oxide (ITO) at a layer thickness of 10 nm to 200 nm. Just before application of the organic layers, this ITO layer, particularly after an extended storage time, is to be treated in an ultrasound bath first with pure acetone and then with methanol. After blowing off insoluble particles with a jet of vaporizable $CO_2$ ice crystals, the layer is subsequently also treated with oxygen plasma, wherein organic contaminations are burnt and removed.

Also according to the state of the art, the hole transport layer 3 (HTL) can be prepared with the spin coating technique. The hole transport layer 3 consists e.g. of a molecular dispersion of N,N'-diphenyl-N,N'-bis-(3-methylphenyl)-1, 1'-biphenyl-4,4'-diamine (TPD) in poly-(N-vinylcarbazol) (PVK) or a suitable polycarbonate at a weight ratio of 1:1, wherein the ratio of hole transport material to hole-transporting binding agents or also to an insulating binding agent, such as polycarbonate, can vary within a broad range. Initially a clear solution of PVK/TPD is prepared in an organic solvent or solvent mixture, such as e.g. methylene chloride, according to conventional method, while stirring in a solvent container, as well as inert gas at room temperature and, subsequently, the electrically conductive transparent substrate is coated with a spin coating device in such a way that the hole transport layer 3 upon drying at 25° C. to 40° C. with inert gas, for example, in a vacuum drying chamber with a dry layer thickness of 50 to 80 ml. It should be mentioned that the hole transport layer 3, according to the state of the art of technology, consisting preferably of N,N'-diphenyl-N,N'-bis-(3-methylphenyl)-1,1'-biphenyl-4, 4'-diamine (TPD) or N,N'-biphenyl-N,N'-bis-(1-naphthyl)-benzidine (1-NPB), can also be applied onto the conductive carrier through vacuum metallizing.

Subsequently, in a high vacuum, a dye pursuant to the invention is applied onto this layer as a luminescent compound either alone or as doping agent, individually or in the form of a mixture with different doping agents, using the co-vaporization technique along with the luminescent compound, e.g. together with $AlQ_3$. The concentration of the doping agent or also of a doping agent mixture, referred to the weight of the luminescent compound $AlQ_3$, can be in the concentration range of 1 percent by weight to 8 percent by weight, preferably 1.5 percent by weight to 3 percent by weight.

Depending on the application purpose of the electroluminescent device, the concentration of the different doping agent, when using a mixture of doping agents can vary within a broad range, for example, between 0.1 percent by weight and 50 percent by weight, with respect to the overall weight of all doping agents.

And finally, without intermediate ventilation, the metal cathode 1 is applied through co-vaporization of Mg/Ag, generally at the ratio of 10:1, preferably, however, through vaporization of Li-benzoate and Al (0.7 nm Li-benzoate plus 100 nm Al). However other metals, such as silver, magnesium, calcium or indium, alloys thereof or other ratios of the metals or alloys can also be used.

Very efficient red electroluminescent devices can also be obtained when, in the luminescent layer 2, the compounds 1 through 6 listed in Table I are used preferably as new doping agents, which have not been known for these purposes until now, either individually or also in a mixture for the doping of $AlQ_3$ (the quantity ratio of equivalent doping agents can be selected freely).

Very efficient red electroluminescent devices are also obtained when the new doping agents, or also mixtures thereof are co-vaporized with a different doping agent (for example dyes pursuant to U.S. Pat. No. 4,769,292), such as with a 1,2- or 1,3-substituted dihydroxycyclobutene-dione dye, are used in the production of the luminescent layer.

The synthesis procedure for the preparation of the dyes made according to the invention, which have been used in particular as doping agents for luminescent combinations, have been known as such for a long time and was referenced extensively by Lemke (Lemke, R.: Chem. Ber. 103, 1970, 1894–1899; Lemke, R.: DE-A-2,345,189; Lemke, R.: Synthesis 1974, 359–361).

The starting substances required for the new dyes or doping agents with the structure I or II, such as e.g. the 1-oxajulolidine, in the case of synthesis of the dyes 7, 8, 11, 19, 20 pursuant to Table 1 are produced from 8-hydroxyquinoline, monochlor acetic acid under reduction conditions in THF through sodium boron hydride according to H. Katayama, M. Ohkoshi: Synthesis 1982, 692–693. The synthesis of the corresponding 9-formyl-1-oxajulolidines occurs subsequently according to familiar formylation procedures (Organikuzn, Organic-Chemical Basic Practicum, 13$^{th}$ Edition, VEB Deutscher Verlag der Wissenschaften Publishing House, Berlin 1974).

The method for preparing 9-formyl-1,7-dithiojulolidine is also known and has been published in U.S. Pat. No. 3,511,831.

Hetero-bridged 1-methyl-vinyl ketones, such as 5-methyl-2H-pyran-3(6H)-one, are produced according to K. Skinnemoen, K. Undheim: Acta Chemica Scandinavica B 34, 1980, 295–297 in a two-stage process from di-(2-propynyl)-ether through the diacetonyl ether reaction stage and subsequently through intra-molecular ring closure.

The corresponding 5-methyl-2H-1-thiopyran-3(6H)-one is gained similarly through diacetonyl thioether through intra-molecular ring closure.

Preferred dyes of the present invention are the compounds listed in the following Table 1. Some of them are dyes, e.g. dye 1, that are already known for non-linear optical applications (NLO) and published in DE 68919989 T2. The generation of very high electric field strengths through the de-localization of electrons in atomic dimensions, for example, as are generally used with lasers, affect non-linear polarization vectors and susceptibility sensors in the hyper-polarized compound, which are taken advantage of in laser radiation of the optical device for the purpose of generating new (higher) frequencies in absorption and reflection (frequency doubling, sum and difference frequencies) and in various effects and applications (Pockels effect, coherent anti-Stokes Raman scattering, two-photon absorption and emission spectroscopy; optical Kerr effect for optical switches and the like).

However since these NLO applications are primarily about absorption properties and the fluorescent properties are not affected, the usage of these familiar compounds for emission applications such as in organic light-emitting device is not evident.

TABLE I

Dye 1

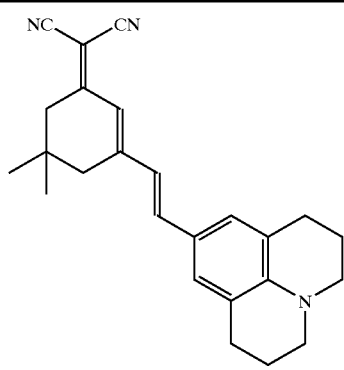

TABLE I-continued

Dye 2

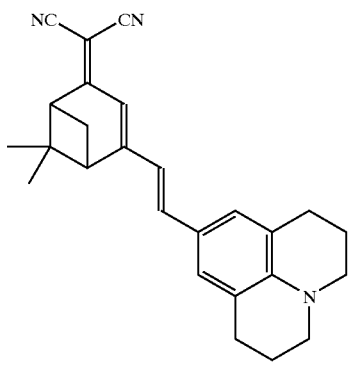

Dye 3

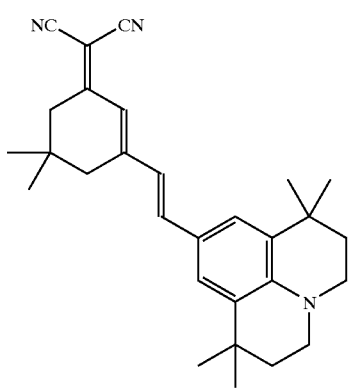

Dye 4

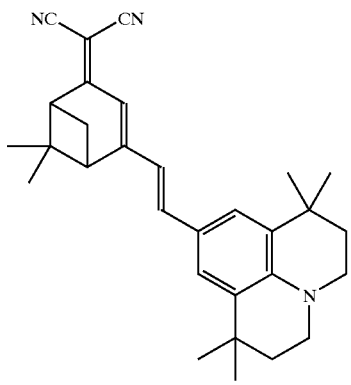

Dye 5

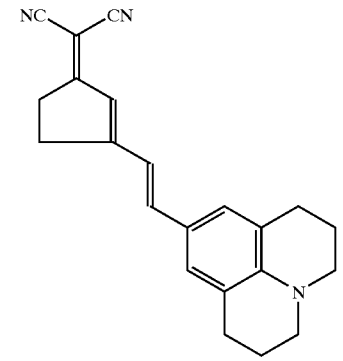

TABLE I-continued
| Dye 6 | 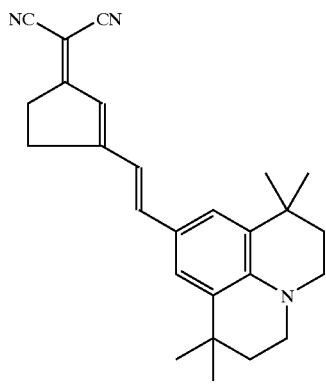 |
| --- | --- |
| Dye 7 | 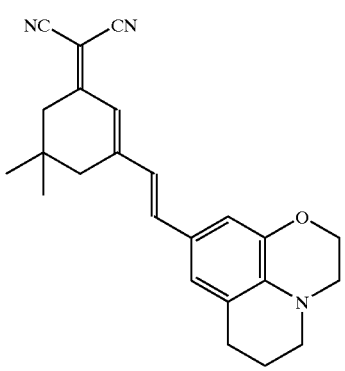 |
| Dye 8 | 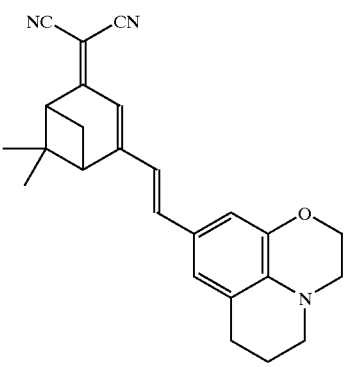 |
| Dye 9 | 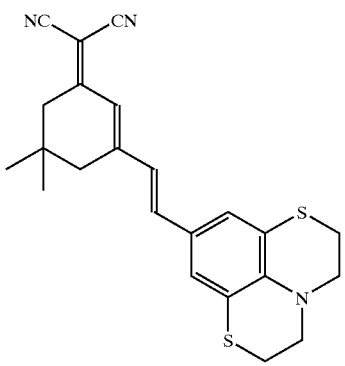 |
TABLE I-continued
| Dye 10 | 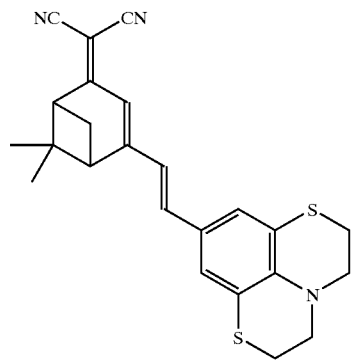 |
| --- | --- |
| Dye 11 | 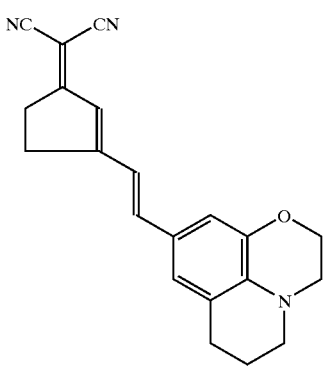 |
| Dye 12 | 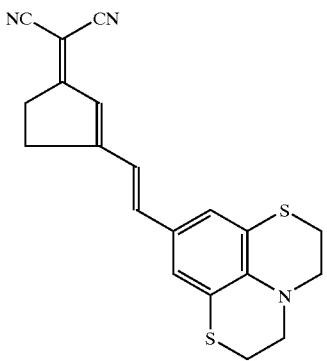 |
| Dye 13 | 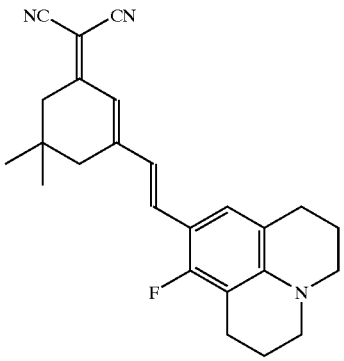 |

TABLE I-continued

| Dye 14 | (structure) |
| Dye 15 | (structure) |
| Dye 16 | (structure) |
| Dye 17 | (structure) |
| Dye 18 | (structure) |
| Dye 19 | (structure) |
| Dye 20 | (structure) |
| Dye 21 | (structure) |

TABLE I-continued

Dye 22

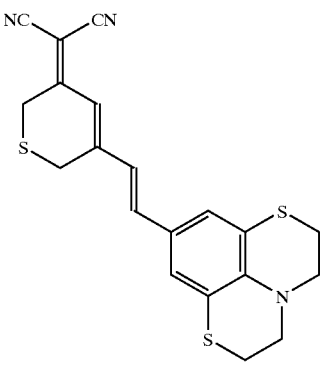

The following examples serve the purpose of explaining the invention in more detail, however, the invention is not limited to these examples.

EXAMPLE 1

(general synthesis example): For the preparation of the dyes that are to be used pursuant to this invention, 11 mmol of a cyclic 1-methyl-vinyl ketone (isophoron, verbenon, 5-methyl-2H-pyran-3(6H)-one, 5-methyl-2H-thiopyran-3 (6H)-one and the like), 0.66 g (10 mmol) malonitril and 0.5 g piperidine in 10 ml dimethylformamide are placed in a 50 ml three-necked flask, equipped with a thermometer and magnetic stirrer, and warmed initially for 1 hour at 25° C. while stiffing. Afterwards, the mixture is heated for another hour at a temperature of 80° C. The reaction mixture takes on an increasingly brown color. Now, 10 mmol of the corresponding 9-formyljulolidine e.g. 9-formyl-8-fluor-1,1, 7,7-tetramethyljulolidine, 9-formyl-1,7-dithiojulolidine or 9-formyl-1-oxajulolidine, as solid matter or also in solution, are added in several portions to the hot reaction mixture while stirring and it is heated again for 1 hour at 80° C. The color of the reaction mixture changes to a deep red violet. The reaction process is observed through thin-layer chromatography (silica gel 60, running agent mixture: 1-butanol/ethanol/acetic acid/water 60/10/5120). After the respective dye has been formed in the desired quantity, the reaction is stopped. The mixture is allowed to cool down and sit overnight, whereupon the crystallisate is vacuumed off, rinsed several times with methanol, to remove any non-reacted portions of the starting substance, and dried at 60° C. in a vacuum drying chamber for 8 hours. Dyes that do not crystallize right away are brought to crystallization by adding to the reaction solution a precipitating agent, such as e.g. methanol.

Cleaning of the dyes generally occurs through re-crystallization, for example from methanol, and subsequent sublimation in a high vacuum.

EXAMPLE 2

On a glass carrier 5 coated with ITO (indium tin oxide) 4 pursuant to FIG. 1 a hole transport layer (HTL) 3 was applied through the spin coating of a solution of N,N'-diphenyl-N,N'-bis-(3-methylphenyl)-benzidine mixed with poly-(N-vinylcarbazol) 1:1 (parts by weight) in dichlormethane. Upon drying the layer under inert gas at a temperature between 25° C. and 40° C., the layer thickness is 50 nm. Then, in a high vacuum ($10^{-5}$ hPa), the electroluminescence layer 2 is applied through co-vaporization of $AlQ_3$ on the hole transport layer 3 obtained this way and the cleaned dye 1 in a concentration of 1.5 percent by weight, with respect to $AlQ_3$. Subsequently, the metal cathode 1 is applied through the vaporization of LiF and Al (0.7 nm Li-fluoride+100 nm Al). The procedure for the metal cathode can also occur in a fashion corresponding to example 3.

For the purpose of measuring the electroluminescence, a controlled tension of between 1 and 20V is applied between the ITO and metal electrodes. The device obtained this way produces a luminance of up to 580 cd/m² at 12.6V. The emitted light is free from secondary emissions of the $AlQ_3$ in the range around 530 nm and visually exhibits a very pure red color tone.

EXAMPLE 3

On a glass carrier 5 coated with ITO (indium tin oxide) 4, pursuant to FIG. 1 a hole transport layer (HTL) 3 made of N,N'-diphenyl-N,N'-bis-(3-methylphenyl)-benzidine at a layer thickness of 50 nm is applied through vapor deposition in a high vacuum ($10^{-5}$ hPa). On the hole transport layer 3 obtained this way, the electroluminescence layer 2 is then applied through co-vaporization of $AlQ_3$ and the cleaned dye 1 at a concentration of 2 percent by weight, with respect to $AlQ_3$. The thickness of the applied electroluminescence layer 2 is 60 nm. Subsequently the metal cathode 1 is applied through the vaporization of Li-benzoate and Al (0.7 nm Li-benzoate+100 nm Al).

For the purpose of measuring the electroluminescence, a controlled tension between 1 and 20V has been applied between the ITO and metal electrodes. The device obtained this way produces a luminance of up to 600 cd/m² at 12.8V. The emitted light is free from secondary emissions of the $AlQ_3$ in the range around 530 nm and visually exhibits a very pure red color tone.

EXAMPLE 4

On a glass carrier 5 coated with ITO (indium tin oxide) 4, pursuant to FIG. 2 a hole transport layer (HTL) 3 made of 4,4',4"-tris-(N-(1-naphthyl)-N-phenyl-amino)-triphenylamine at a layer thickness of 55 run was applied through vapor deposition in a high vacuum ($10^{-5}$ hPa). On the hole transport layer 3 obtained this way then the luminescent layer 2 is applied through co-vaporization of $AlQ_3$ and the cleaned dye 1 at a concentration of 1.5 percent by weight, referred to $AlQ_3$. The thickness of the applied luminescent layer 2 is 30 nm. Onto this layer, now 10 nm $AlQ_3$ are applied through vapor deposition as the electron transport layer 6. Subsequently the metal cathode 1 is applied through the vaporization of LiF and Al (0.7 nm LiF+100 nm AL). The procedure for the metal cathode can also occur in a fashion corresponding to example 3.

For the purpose of measuring the electroluminescence, a controlled tension between 1 and 15V has been applied between the ITO and metal electrodes. The device obtained this way produces a luminance of up to 900 cd/m² at 14V. The emitted light is free from secondary emissions of the $AlQ_3$ in the range around 530 run and visually exhibits a very pure red color tone.

EXAMPLE 5

On a glass carrier 5 coated with ITO (indium tin oxide) 4, a 5 nm thick hole injection layer made of CuPC, a hole transport layer (HTL) 3b made of 4,4',4"-tris-N-(1-naphthyl)-N-phenyl-amino)-triphenylainine at a layer thickness of 55 mm and one additional hole transport layer 3a made of N,N'-biphenyl-N,N'-bis-(1-naphthylybenzidine (1-NPB) at a layer thickness of 5 nm are applied through vapor deposition in a high vacuum (105 hPa). On the hole transport layers 3a, 3b obtained this way then the luminescent layer 2 is applied through co-vaporization of $AlQ_3$ and the cleaned dye 1 at a concentration of 2 percent by weight, referred to $AlQ_3$. The thickness of the applied luminescent layer 2 is 40 nm. Onto this layer, now 5 nm $AlQ_3$ are applied through vapor deposition as the electron transport layer 6. Subsequently the metal cathode 1 is applied through the vaporization of Li-benzoate and Al (0.7 nm Li-benzoate+ 100 rim Al).

For the purpose of measuring the electroluminescence, a controlled tension between 1 and 15V has been applied between the ITO and metal electrodes. The device obtained this way produces a luminance of up to 2,050 $cd/m^2$ at 14.0V. The emitted light is free from secondary emissions of the $AlQ_3$ in the range around 530 run and visually exhibits a very pure red color tone.

EXAMPLE 6

Analogous to the layer structure in example 5, the luminescent layer 2 is applied onto the hole transport layers 3a, 3b through co-vaporization of $AlQ_3$ and dye 1, wherein it is used at a concentration of only 0.7 percent by weight (under-doping) referred to $AlQ_3$, then an electroluminescent device is obtained, which emits alternatively white light at a tension of 17V that is applied between the ITO and metal electrodes.

EXAMPLE 7

On a glass carrier 5 coated with ITO (indium-tin-oxide) 4, a 5 nm thick hole injection layer made of CuPC, a hole transport layer (HTL) 3b made of 4,4',4''-tris-(N-(1-naphthyl)-N-phenyl-amino)-triphenylamine at a layer thickness of 55 nm and another hole transport layer 3a made of N,N'-biphenyl-N,N'-bis-(1-naphthyl)benzidine (1-NPB) at a layer thickness of 5 nm are applied successively through vapor deposition in a high vacuum ($10^{-5}$ hPa). On the hole transport layers 3a, 3b obtained this way then the luminescent layer 2 is applied through co-vaporization of $AlQ_3$ and the cleaned dye 14 at a concentration of 2.5 percent by weight, with respect to $AlQ_3$. The thickness of the applied luminescent layer 2 is 40 nm. Onto this layer, now 5 nm $AlQ_3$ are applied through vapor deposition as the electron transport layer 6. Subsequently the metal cathode 1 is applied through the vaporization of Li-benzoate and Al (0.7 nm Li-benzoate+100 nm AL).

For the purpose of measuring the electroluminescence, a controlled tension between 1 and 15V has been applied between the ITO and metal electrodes. The device obtained this way produces a luminance of up to 2,000 $cd/m^2$ at 13.8V. The emitted light is free for secondary emissions of the $AlQ_3$ in the range around 530 nm and visually exhibits a very pure red color tone.

EXAMPLE 8

If analogue to the layer structure of example 7 the luminescent layer 2 is applied onto the hole transport layers 3a, 3b through co-vaporization of $AlQ_3$ and dye 14, wherein it is used at a concentration of only 0.6 percent by weight (under-doping) referred to $AlQ_3$, then an electroluminescent device is obtained, which emits alternatively white light at a tension of 17V that is applied between the ITO and metal electrodes.

What is claimed is:
1. A compound having formula VII:

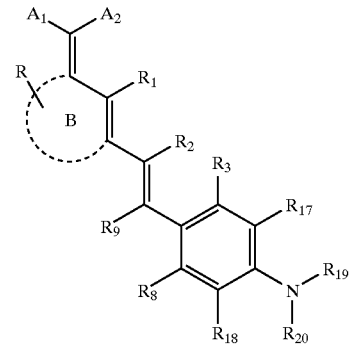

VII wherein B is an unsaturated carbocyclic 4–8 member ring, wherein if B is a 6–8-member ring, the ring optionally includes two C-atoms that form a bridge with each other, radicals R are one or more substituents, which can be the same or different and are hydrogen or a straight-chain or branched $C_1$–$C_6$-alkyl group:

$R_1$, $R_2$, and $R_9$ are the same or different and are hydrogen, halogen, or straight-chain or branched $C_1$–$C_6$-alkyl groups;

$R_3$ is hydrogen, a straight-chain or branched $C_3$–$C_6$-alkyl group, —$OR_{16}$, —$COOR_{16}$, N,N-dialkylamino, acetylamino, or halogen, wherein $R_{16}$ is hydrogen or a straight-chain or branched $C_1$–$C_6$-alkyl group;

$R_8$ is halogen;

$R_{17}$ and $R_{18}$ are the same or different and are hydrogen, halogen, or a straight-chain or branched $C_1$–$C_6$-alkyl group; $R_{19}$ and $R_{20}$ are the same or different and are hydrogen or a straight-chain or branched $C_1$–$C_6$-alkyl group; or at least one of the substituent pairs $R_{17}/R_{19}$ and $R_{18}$ $R_{20}$ link together to form an alicyclic ring; or the substituent pair $R_{19}/R_{20}$ link together to form a heterocyclic ring together with the nitrogen atom; and $A_1$ and $A_2$ are the same or different and are cyano, nitro, or —$COOR_{16}$, wherein $R_{16}$ is hydrogen or a straight-chain or branched $C_1$–$C_6$-alkyl group.

2. The compound of claim 1 having formula V:

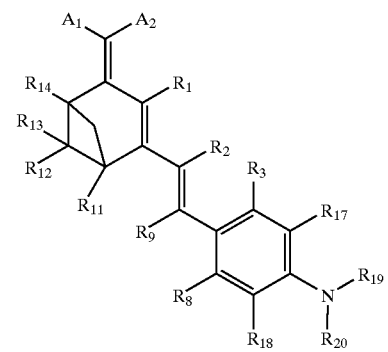

V wherein $R_1$, $R_2$, $R_3$, $R_8$, $R_9$, $R_{17}$, $R_{18}$, $R_{19}$, $R_{20}$, $A_1$, and $A_2$ are as defined in claim 1; and $R_{11}$, $R_{12}$, $R_{13}$ and $R_{14}$ are the same or different and are hydrogen or straight-chain or branched $C_1$–$C_6$-alkyl groups.

3. The compound of claim 1 having formula VI:

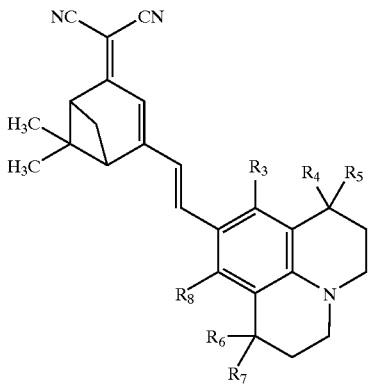

VI wherein $R_3$ and $R_8$ are as defined in claim 1; and
wherein $R_4$, $R_5$, $R_6$, and $R_7$ are the same and are hydrogen or methyl.

4. The compound of claim 1, wherein B is a six-member, unsaturated carbocyclic ring, optionally substituted by one or more straight-chain or branched $C_1$–$C_6$-alkyl groups, and two ring atoms in 1,3-positions of the ring form an alicyclic bridge with each other such that the unsaturated carbocyclic B ring has a formula:

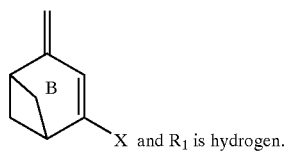

X and $R_1$ is hydrogen.

5. The compound of claim 4, wherein the straight chain or branched chain $C_1$–$C_6$-alkyl groups are the same or different and each are methyl, isopropyl, or tert-butyl.

6. A compound having formula VIII:

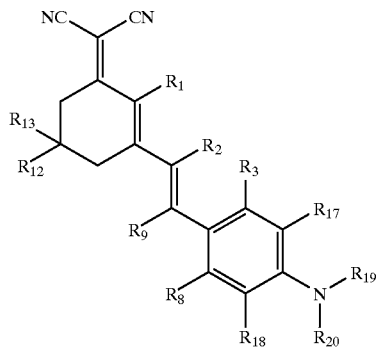

VIII wherein $R_1$, $R_2$, and $R_9$ are the same or different and are hydrogen or methyl;
$R_3$ is hydrogen or halogen;
$R_8$ is halogen:
$R_{12}$ and $R_{13}$ are the same or different and are hydrogen or a straight-chain or branched $C_1$–$C_6$-alkyl group; and
$R_{17}$ and $R_{18}$ are the same or different and are hydrogen, fluorine, or a straight-chain or branched $C_1$–$C_6$-alkyl group; $R_{19}$ and $R_{20}$ are the same or different and are hydrogen or a straight-chain or branched $C_1$–$C_6$-alkyl group; or at least one of the substituent pairs $R_{17}$/$R_{19}$ and $R_{19}$/$R_{20}$ link together to form an alicyclic ring; or the substituent pair $R_{19}$/$R_{20}$ link together to form a heterocyclic ring together with the nitrogen atom.

7. The compound of claim 6,
wherein $R_1$, $R_2$, and $R_9$ are hydrogen.

8. The compound of claim 6,
wherein $R_1$, $R_2$, and $R_9$ are hydrogen;
$R_{12}$ and $R_{13}$ are methyl;
$R_3$ is hydrogen or fluorine; and
$R_8$ is fluorine.

9. The compound of claim 6 having formula IX:

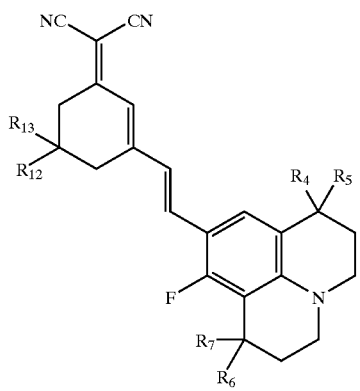

IX wherein $R_4$, $R_5$, $R_6$, and $R_7$ are the same and are hydrogen or methyl; and
$R_{12}$ and $R_{13}$ are the same or different and are a straight chain or branched $C_1$–$C_6$-alkyl group.

10. The compound of claim 6 having formula XI:

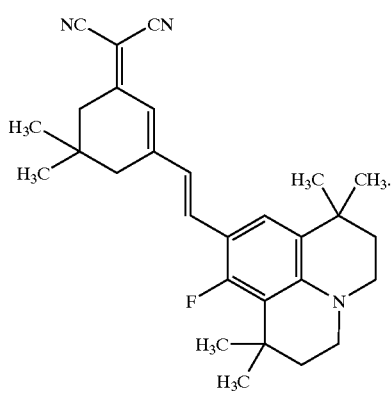

XI

11. The compound of claim 6 having formula XII:

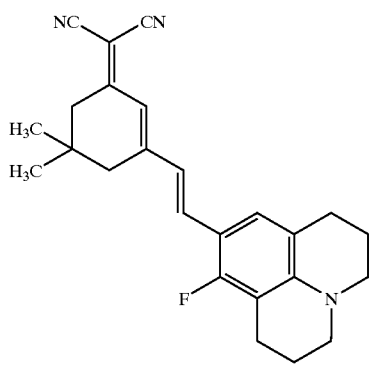

XII

12. The compound of claim 6 having formula XIII:

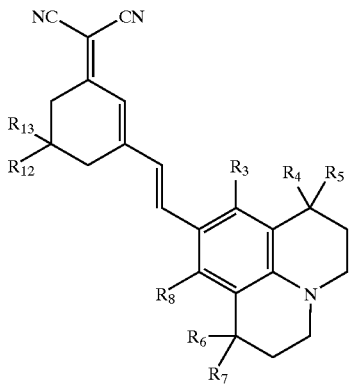

XIII wherein $R_3$, $R_8$, $R_{12}$, and $R_{13}$, are as defined in claim 6; and $R_4$, $R_5$, $R_6$ and $R_7$ are the same or different and are hydrogen or a straight-chain or branched $C_1$–$C_6$-alkyl group.

13. The compound of claim 12, wherein $R_4$, $R_5$, $R_6$, and $R_7$ are the same and are hydrogen or methyl.

14. The compound of claim 12, wherein $R_3$ is hydrogen; $R_4$, $R_5$, $R_6$, and $R_7$ are the same or different and are a straight-chain or branched $C_1$–$C_6$-alkyl group; and $R_8$ is fluourine.

15. The compound of claim 12, wherein $R_4$, $R_5$, $R_6$, and $R_7$ are methyl; and at least one of $R_3$ and $R_4$ is fluorine.

16. The compound of claim 15, wherein $R_{12}$ and $R_{13}$ are methyl.

17. The compound of claim 6, wherein $R_8$ is fluorine.

18. The compound of claim 6, wherein substituent pair $R_{17}/R_{19}$ and substituent pair $R_{18}/R_{20}$ each link together to form 6-member rings, which are substituted by hydrogen and optionally one or more $C_1$–$C_6$-alkyl groups.

19. A compound of formula II:

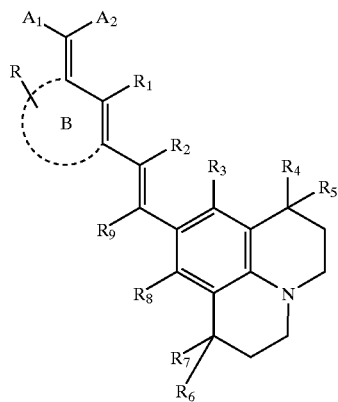

II wherein B is an unsaturated carbocyclic 4–8 member ring, wherein if B is a 6–8-member ring, the ring optionally includes two C-atoms that form a bridge with each other;

radicals R are one or more substituents, which can be the same or different and are hydrogen or straight-chain or branched $C_1$–$C_6$-alkyl groups;

$R_1$, $R_2$, and $R_9$ are the same or different and are hydrogen, halogen, or straight-chain or branched $C_1$–$C_6$-alkyl groups;

$R_3$ is hydrogen, a straight-chain or branched $C_1$–$C_6$-alkyl group, —$OR_{16}$, —$COOR_{16}$, N,N-dialkylamino, acetylamino, or halogen, wherein $R_{16}$ is hydrogen or a straight-chain or branched $C_1$–$C_6$-alkyl group;

$R_4$, $R_5$, $R_6$, and $R_7$, are the same or different and are straight-chain or branched $C_1$–$C_6$-alkyl groups;

$R_8$ is halogen; and $A_1$ and $A_2$ are the same or different and are cyano, nitro, or —$COOR_{16}$, wherein $R_{16}$ is hydrogen or a straight-chain or branched $C_1$–$C_6$-alkyl group.

20. An electro-luminescent device, comprising a hole transport layer and a luminescent layer between two conductive electrodes, wherein the luminescent layer comprises, as a luminescent compound or doping agent for a luminescent compound, at least one compound of formula VII:

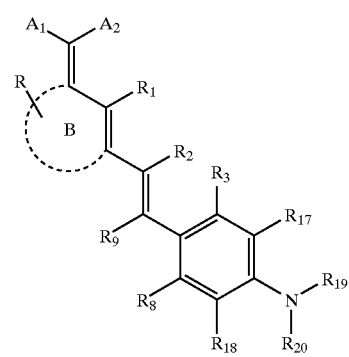

VII wherein B is an unsaturated carbocyclic 4–8 member ring, wherein if B is a 6–8-member ring, the ring optionally includes two C-atoms that form a bridge with each other;

radicals R are one or more substituents, which can be the same or different and are hydrogen or a straight-chain or branched $C_1$–$C_6$-alkyl group;

$R_1$, $R_2$, and $R_9$ are the same or different and are hydrogen, halogen, or straight-chain or branched $C_1$–$C_6$-alkyl groups;

$R_3$ is hydrogen, a straight-chain or branched $C_1$–$C_6$-alkyl group, —$OR_{16}$, —$COOR_{16}$, N,N-dialkylamino, acetylamino, or halogen, wherein $R_{16}$ is hydrogen or a straight-chain or branched $C_1$–$C_6$-alkyl group;

$R_8$ is halogen;

$R_{17}$ and $R_{18}$ are or different and are hydrogen, halogen, or a straight-chain or branched $C_1$–$C_6$-alkyl group; $R_{19}$ and $R_{20}$ are the same or different and are hydrogen or a straight-chain or branched $C_1$–$C_6$-alkyl group; or at least one of the substituent pairs $R_{17}/R_{19}$ and $R_{18}/R_{20}$ link together to form an alicyclic ring; or the substituent pair $R_{19}/R_{20}$ link together to form a heterocyclic ring together with the nitrogen atom; and $A_1$ and $A_2$ are the same or different and are cyano, nitro, or $COOR_{16}$, wherein $R_{16}$ is hydrogen or a straight-chain or branched $C_1$–$C_6$-alkyl group.

21. An electro-luminescent device, comprising a hole transport layer and a luminescent layer between two conductive electrodes, wherein the luminescent layer comprises, as a luminescent compound or doping agent for a luminescent compound, at least one compound of formula I:

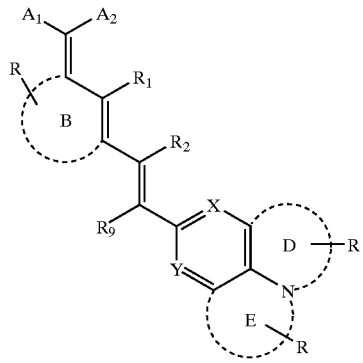

I wherein B is an unsaturated carbocyclic 4–8-member ring and B optionally is a 6–8-member ring that includes two C-atoms that form a bridge with each other, D and E are 5- or 6-member rings, which optionally include one additional hetero-atom selected from N, O, and S;

radicals R are one or more substituents, which can be the same or different and are hydrogen or a straight-chain or branched $C_1$–$C_6$-alkyl group;

X is nitrogen or C—$R_3$ and Y is nitrogen or C—$R_8$;

$R_3$ is hydrogen, a straight-chain or branched $C_1$–$C_6$-alkyl group, hydroxy, —$OR_{16}$, —$COOR_{16}$, N,N-dialkylamino, acetylamino, or halogen, wherein $R_{16}$ is hydrogen, or a straight-chain or branched $C_1$–$C_6$-alkyl group;

$R_8$ is halogen.

$R_1$, $R_2$ and $R_9$ are the same or different and are hydrogen, straight-chain or branched $C_1$–$C_6$-alkyl groups, or halogen;

one or more of substituent pairs $R_1/R_2$, $R_2/R_3$, and $R_8/R_9$ optionally link together to form an alicyclic, or aromatic ring; and $A_1$ and $A_2$ are the same or different and each is cyano, nitro, or —$COOR_{16}$, wherein $R_{16}$ is hydrogen or a straight-chain or branched $C_1$–$C_6$-alkyl group.

22. The device of claim 21, wherein the compound of formula I includes at least one compound of formula II:

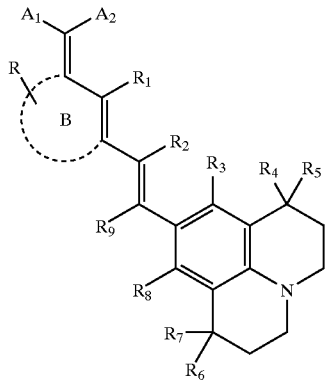

II wherein B, R, $R_1$, $R_2$, $R_3$, $R_8$, $R_9$, $A_1$, and $A_2$ are as defined in claim 21; and $R_4$, $R_5$, $R_6$, and $R_7$, are the same or different and are straight-chain or branched $C_1$–$C_6$alkyl groups.

23. The device of claim 21, wherein the straight chain or branched chain $C_1$–$C_6$-alkyl groups are the same or different and are methyl, isopropyl, or tert-butyl.

24. The device of claim 21, wherein the luminescent layer further comprises one or more doping agents selected from the group consisting of 2-alkyl-6-N,N-dialkylaminostyryl-substituted 4-dicyanomethylene-4-H-pyran, julolidine-substituted 4-dicyanomethylene-4-H-pyran, and 3-(dicyanomethylene)-5,5-dimethyl-4-N,N-dimethylaminostyryl)cyclohexane.

25. The device of claim 24, wherein the 2-alkyl-6-N,N-dialkylaminostyryl-substituted 4-dicyanomethylene-4-H-pyran and the julolidine-substituted 4-dicyanomethylene-4-H-pyran are substituted with tert-butyl on the pyran ring.

26. The device of claim 21, wherein the luminescent layer further comprises a 1,2- or 1-3-substituted dihydroxycyclobutene-dione dye.

27. The device of claim 21, wherein the luminescent layer further comprises tris-(8-hydroxyquinolino)-aluminum ($AlQ_3$) or a compound that includes 1,3,4-oxadiazol or distyryl-aryl.

28. The device of claim 21, wherein the luminescent layer comprises:

$AlQ_3$ as a luminescent compound; and a doping agent, which includes at least one compound of the formula 1; and the luminescent layer has a concentration of the doping agent between 1% by weight and 8% by weight in relation to $AlQ_3$.

29. The device of claim 28, wherein the luminescent layer has a concentration of the doping agent between 1.5% by weight and 3% by weight in relation to $AlQ_3$.

30. The device of claim 28, wherein the device generates a red light emission.

31. The device of claim 30, wherein the device has a luminance in the range of 580–2,050 cd/$m^2$ at 10–12V.

32. The device of claim 30, wherein the device emits red light without secondary emission of $AlQ_3$ at 530 nm.

33. The device of claim 21, wherein the device emits white light and the luminescent layer comprises:

$AlQ_3$ as a luminescent compound; and a doping agent, which includes at least one compound of the formula I; and the luminescent layer has a concentration of the doping agent between 0.1% by weight and 1% by weight in relation to $AlQ_3$.

34. A compound having formula II:

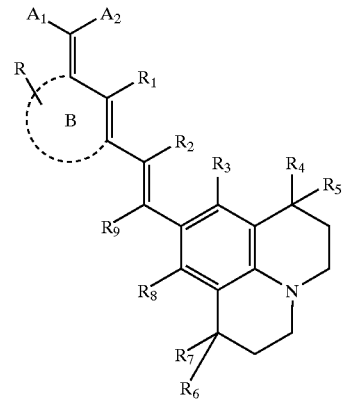

II wherein B is an unsaturated 5–6 member carbocyclic ring, wherein B optionally is a 6-member ring that includes two C-atoms that form a bridge with each other;

radicals R are one or more substituents, which can be the same or different and are hydrogen or a straight-chain or branched $C_1$–$C_6$-alkyl group;

$R_1$, $R_2$, and $R_9$ are the same or different and are hydrogen, or straight-chain or branched $C_1$–$C_6$-alkyl groups;

$R_3$ is hydrogen, a straight-chain or branched $C_1$–$C_6$-alkyl group, —$OR_{16}$, —$COOR_{16}$, N,N-dialkylamino, acetylamino, or halogen, wherein $R_{16}$ is hydrogen or a straight-chain or branched $C_1$–$C_6$-alkyl group;

$R_8$ is halogen;

$R_4$, $R_5$, $R_6$ and $R_7$ are the same or different and are hydrogen or a straight-chain or branched $C_1$–$C_6$-alkyl group; and $A_1$ and $A_2$ are the same or different and are cyano, nitro, or $COOR_{16}$, wherein $R_{16}$ is hydrogen or a straight-chain or branched $C_1$–$C_6$-alkyl group.

35. An electroluminescent device comprising a luminescent layer which includes at least one compound having formula:

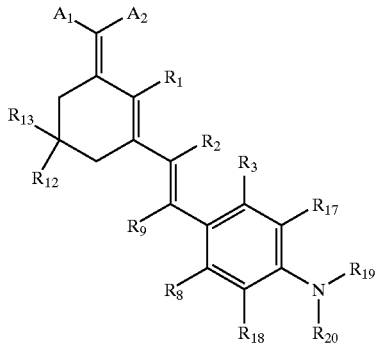

wherein $R_1$, $R_2$, and $R_9$ are the same or different and are hydrogen or methyl;

$R_3$ is hydrogen or halogen;

$R_8$ is halogen;

$R_{12}$ and $R_{13}$ are the same or different and are hydrogen or a straight-chain or branched $C_1$–$C_6$-alkyl group;

$R_{17}$ and $R_{18}$ are the same or different and are hydrogen, fluorine, or a straight-chain or branched $C_1$–$C_6$-alkyl group; $R_{19}$ and $R_{20}$ are the same or different and are hydrogen or a straight-chain or branched $C_1$–$C_6$-alkyl group; or at least one of the substituent pairs $R_{17}/R_{19}$ and $R_{18}/R_{20}$ link together to form an alicyclic ring; or the substituent pair $R_{19}/R_{20}$ link together to form a heterocyclic ring together with the nitrogen atom; and $A_1$ and $A_2$ are the same or different and are cyano, nitro, or $COOR_{16}$, wherein $R_{16}$ is hydrogen or a straight-chain or branched $C_1$–$C_6$-alkyl group.

36. The device of claim 35, wherein $R_1$, $R_2$, and $R_9$ are hydrogen;

$R_{12}$ and $R_{13}$ are methyl;

$R_3$ is hydrogen or fluorine; and $R_8$ is fluorine.

37. The device of claim 35, wherein the luminescent layer comprises at least one compound having formula IX:

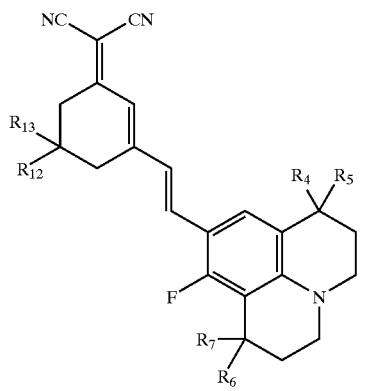

wherein $R_4$, $R_5$, $R_6$, and $R_7$ are the same and are hydrogen or methyl; and $R_{12}$ and $R_{13}$ are the same or different and are a straight chain or branched $C_1$–$C_6$-alkyl group.

38. The device of claim 35, wherein the luminescent layer comprises a compound having formula XI:

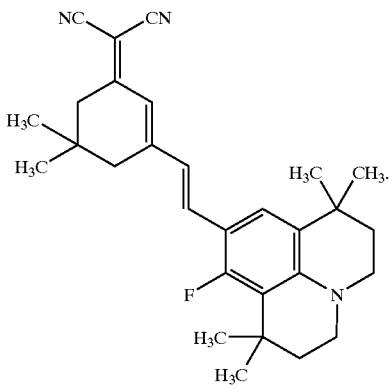

39. The device of claim 35, wherein the luminescent layer comprises a compound having formula XII:

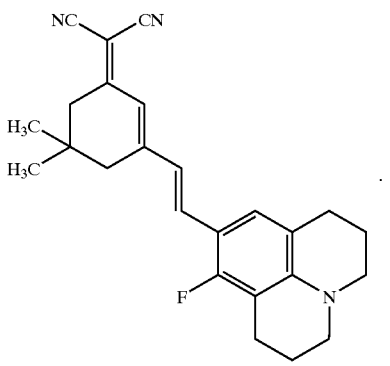

40. The device of claim 35, wherein the luminescent layer comprises at least one compound having formula XIII:

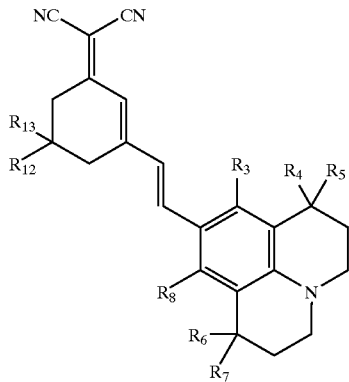

wherein $R_3$, $R_8$, $R_{12}$, and $R_{13}$, are as defined in claim 35; and $R_4$, $R_5$, $R_6$ and $R_7$ are the same or different and are hydrogen or a straight-chain or branched $C_1$–$C_6$-alkyl group.

41. The device of claim 35, wherein $R_8$ is fluorine.

42. The device of claim 35, wherein substituent pair $R_{17}/R_{19}$ and substituent pair $R_{18}/R_{20}$ each link together to form 6-member rings, which are substituted by hydrogen and optionally one or more $C_1$–$C_6$-alkyl groups.

43. A compound having formula I:

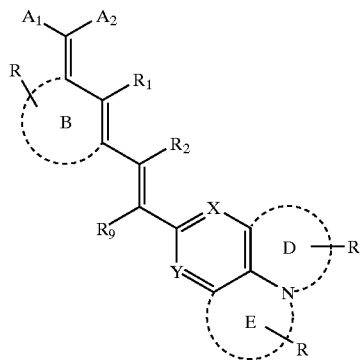

wherein B is an unsaturated carbocyclic 48-member ring and B optionally is a 6–8-member ring that includes two C-atoms that form a bridge with each other;

D and E are 5- or 6-member rings, which optionally include one additional heteroatom selected from N, O, and S;

radicals R are one or more substituents, which can be the same or different and are hydrogen or a straight-chain or branched $C_1$–$C_6$-alkyl group;

X is nitrogen or C—$R_3$ and Y is nitrogen or C—$R_3$;

$R_3$ is hydrogen, a straight-chain or branched $C_1$–$C_6$-alkyl group, hydroxy, —$OR_{16}$, —$COOR_{16}$, N,N-dialkylamino, acetylamino, or halogen, wherein $R_{16}$ is hydrogen, or a straight-chain or branched $C_1$–$C_6$-alkyl group;

$R_8$ is halogen;

$R_1$, $R_2$ and $R_9$ are the same or different and are hydrogen, straight-chain or branched $C_1$–$C_6$-alkyl groups, or halogen;

one or more of substituent pairs $R_1/R_2$, $R_2/R_3$, and $R_8/R_9$ optionally link together to form an alicyclic, heterocyclic, or aromatic ring; and $A_1$ and $A_2$ are the same or different and each is cyano, nitro, or $COOR_{16}$, wherein $R_{16}$ is hydrogen or a straight-chain or branched $C_1$–$C_6$-alkyl group.

* * * * *

UNITED STATES PATENT AND TRADEMARK OFFICE
CERTIFICATE OF CORRECTION

PATENT NO.    : 6,844,089 B2
DATED         : January 18, 2005
INVENTOR(S)   : Dr. Andreas Richter, Dietmar Keil and Dr. Gerhard Diener It is certified that error appears in the above-identified patent and that said Letters Patent is hereby corrected as shown below:

Column 18,
Line 29, after "straight-chain or branched" please delete "$C_3$-$C_6$" and insert -- $C_1$-$C_6$ --.
Line 39, please delete "$R_{18}$ $R_{20}$" and insert -- $R_{18}/R_{20}$ --.

Column 19,
Line 32, after 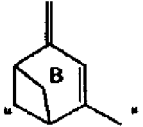 please delete "$X$ and $R_1$ is hydrogen."

Line 33, please insert -- and $R_1$ is hydrogen. --.
Line 64, please delete "$R_{19}/R_{20}$" and insert -- $R_{18}/R_{20}$ --.

Column 21,
Line 29, please delete "fluourine" and insert -- fluorine --.

Column 22,
Line 52, after "$R_{17}$ and $R_{18}$" please delete "are or" and insert -- are the same or --.

Column 23,
Line 37, after "form an alicyclic," please insert -- heterocyclic, --.

Column 24,
Line 4, please replace "3-(dicyanomethylene)-5,5-dimethyl-4-N,N-dimethylamino-"
with -- 3-(dicyanomethylene)-5,5-dimethyl-l-(4-N,N-dimethylamino- --.
Line 20, after "the formula" please delete "1" and insert -- I --.

Column 27,
Line 19, after "carbocyclic" please delete "48-member" and insert -- 4-8-member --.

UNITED STATES PATENT AND TRADEMARK OFFICE
CERTIFICATE OF CORRECTION

PATENT NO. : 6,844,089 B2
DATED : January 18, 2005
INVENTOR(S) : Dr. Andreas Richter, Dietmar Keil and Dr. Gerhard Diener It is certified that error appears in the above-identified patent and that said Letters Patent is hereby corrected as shown below:

Column 28,
Line 4, after "nitrogen or" please delete "$C-R_3$" and insert -- $C-R_8$ --.

Signed and Sealed this

Seventeenth Day of May, 2005

JON W. DUDAS
*Director of the United States Patent and Trademark Office*